United States Patent [19]

Carter et al.

[11] Patent Number: 5,488,855

[45] Date of Patent: Feb. 6, 1996

[54] TESTING LUBRICATING OIL FOR MINERAL OIL CONTAMINANTS

[75] Inventors: Brian H. Carter; Richard S. Rowntree; Andrew P. Swallow, all of Reading, United Kingdom

[73] Assignee: Castrol Limited, Wiltshire, United Kingdom

[21] Appl. No.: 211,537

[22] PCT Filed: Aug. 13, 1993

[86] PCT No.: PCT/GB93/01719

§ 371 Date: Apr. 13, 1994

§ 102(e) Date: Apr. 13, 1994

[87] PCT Pub. No.: WO92/04919

PCT Pub. Date: Mar. 3, 1994

[30] Foreign Application Priority Data

Aug. 14, 1992 [GB] United Kingdom ............... 9217379

[51] Int. Cl.⁶ .................... G01N 15/06; G01N 33/26; F01M 9/02
[52] U.S. Cl. .................... 73/53.05; 73/64.41; 73/61.69
[58] Field of Search .................... 73/64.41, 64.56, 73/61.69, 61.43, 64.56, 61.69, 61.43, 64.41

[56] References Cited

U.S. PATENT DOCUMENTS

| | | | |
|---|---|---|---|
| 2,971,371 | 2/1961 | Brennan et al. | 73/53 |
| 3,003,353 | 10/1961 | Swadesh | 73/73 |
| 3,544,275 | 12/1970 | Habermas | 23/230 |
| 3,681,975 | 8/1972 | Majima et al. | 73/64 |
| 3,861,877 | 1/1975 | Matharani et al. | 23/230 B |
| 4,916,915 | 4/1990 | Flinchbaugh | 62/129 |
| 5,067,455 | 11/1991 | Okajima et al. | 123/196 R |
| 5,313,824 | 5/1994 | Herguth et al. | 73/53.05 |
| 5,396,790 | 3/1995 | Koelliker et al. | 73/61.72 |

FOREIGN PATENT DOCUMENTS

| | | |
|---|---|---|
| 0468729 | 1/1992 | European Pat. Off. . |
| 2145816 | 4/1985 | United Kingdom . |

*Primary Examiner*—Hezron E. Williams
*Assistant Examiner*—J. David Wiggins
*Attorney, Agent, or Firm*—Bacon & Thomas

[57] ABSTRACT

A method of testing for contaminating mineral oil in a sample of synthetic ester lubricating oil from mechanical vapor recompression type heat transfer equipment in a system which is to be retrofilled with hydrohalocarbon working fluid, comprises mixing a predetermined quantity of the synthetic ester lubricating oil with a predetermined quantity of a polar liquid or a mixture of polar liquids and determining whether the resulting mixture is clear or turbid, an optically clear mixture indicating non-saturation by the contaminating mineral oil and that the concentration of contaminating mineral oil in the synthetic ester lubricant is below the maximum tolerable concentration and that the system can therefore be safely retrofilled with the hydrohalocarbon working fluid; and an optically turbid mixture indicating saturation by the contaminating mineral oil and that the concentration of contaminating mineral oil is above the maximum tolerable concentration and that the system must therefore be reflushed with synthetic ester lubricant to further reduce the mineral oil contamination.

13 Claims, No Drawings

TESTING LUBRICATING OIL FOR MINERAL OIL CONTAMINANTS

This invention relates to a method of testing, and in particular to a method of testing to be used in conjunction with the so-called "retrofilling" of mechanical vapour recompression type heat transfer devices.

In recent years there has been increasing concern about the adverse effects of chlorofluorocarbons and hydrofluorocarbons on the content of ozone in the Earth's upper atmosphere and in consequence then is a need to replace the use of the most damaging halocarbons and hydrohalocarbons in refrigeration and air-conditioning systems with the use of more acceptable working fluids, in particular 1,1,1,2-tetrafluoroethane (R134a).

A procedure which has been found to be particularly effective and successful in converting existing recompression type heat transfer devices to use 1,1,1,2-tetrafluoroethane is the retrofill procedure which is described and claimed in EP-A-0 468 729. When the term "retrofill" is used in this application the term is intended to mean the procedure as described and claimed in EP-A-0 468 729.

The synthetic ester lubricating oils which are particularly suited to the retrofill procedure are those which are described in EP-A-0 468 729. These esters are available commercially under the trade name "CASTROL ICEMATIC SW" (Trade Mark), different mixtures of the esters being tailored for particular refrigerant applications, covering a wide range of lubricant viscosities.

In performing the retrofill procedure this usually comprises the steps of isolating the compressor from the remainder of the system, draining the mineral oil to be replaced from the compressor, filling the compressor with a synthetic ester lubricating oil, reconnecting the compressor and then running the system to flush the mineral oil to be replaced back to the compressor. The amount of running which is required will depend on the particular equipment which is to be retrofilled, e.g. the size and complexity of the system. After this running of the system the lubricating oil is tested to check the content of mineral oil whose presence in the system when the working fluid has been replaced by the new hydrofluorocarbon would be likely to cause problems due to the immiscibility of mineral oils in 1,1,1,2-tetrafluoroethane.

The present procedure for testing of samples of the lubricating oil for mineral oil contamination involves sending the sample to a test laboratory where the sample is tested, usually by thin layer chromatography, to determine the mineral oil content of the sample. However, the fact that these tests cannot be performed on the spot by the service engineer so that it is immediately known whether reflushing is required or whether the system is ready for retrofilling with the new hydrohalocarbon is obviously a serious disadvantage. Since the sample may have to be sent some considerable distance and the test procedure itself requires time to be spent by trained personnel, there may be a delay of days before the result is known, and a further visit by the service engineer would therefore be required. There is clearly a need for a simple test procedure which can be performed on the spot by the service engineer who is performing the retrofilling of the refrigeration system which does not require of the service engineer significant chemical skill or knowledge, and so that he/she can very quickly determine whether the system needs to be reflushed before putting in the replacement hydrohalocarbon.

According to the present invention there is provided a method of testing for contaminating mineral oil in a sample of synthetic ester lubricating oil from mechanical vapour recompression type heat transfer equipment which is to be retrofilled with hydrohalocarbon working fluid, which method comprises:

(a) mixing a predetermined quantity of the synthetic ester lubricating oil contaminated with mineral oil with a predetermined quantity of a polar liquid or a mixture of polar liquids, the ester lubricating oil being itself completely miscible with the polar liquid(s) and the resulting mixture having the physical property of manifesting a discontinuous change in optical appearance between turbidity when saturated with mineral oil and clarity when unsaturated with mineral oil; the quantities of the ester lubricating oil and polar liquid(s) being so selected that the mixture is just saturated with the contaminating mineral oil when the concentration of the mineral oil in the synthetic ester lubricant corresponds to the maximum which is tolerable in the equipment after retrofilling with hydrohalocarbon working fluid; and (b) determining whether the resulting mixture is clear or turbid, a clear mixture indicating that the concentration of contaminating mineral oil in the synthetic ester lubricant is below the maximum tolerable concentration and that the equipment can therefore be safely retrofilled with the hydrohalocarbon working fluid; and a turbid mixture indicating that the concentration of contaminating mineral oil is above the maximum tolerable concentration and that the system must therefore be reflushed with synthetic ester lubricant to further reduce the mineral oil contamination.

The present invention also provides a procedure for retrofilling a mechanical vapour recompression type heat transfer system with a hydrohalocarbon working fluid which procedure comprises:

(i) isolating the compressor from the remainder of the system;

(ii) draining the mineral oil from the compressor;

(iii) filling the compressor with a synthetic ester lubricating oil;

(iv) operably reconnecting the compressor to the remainder of the system;

(v) running the system to flush contaminant mineral oil back to and into the compressor, thus diluting the concentration of mineral oil in the compressor and total system;

(vi) extracting a sample of the lubricating oil from the compressor; and (vii) testing the sample of oil by the above method of testing.

The present invention also provides a test kit for use in the above-mentioned method of testing and refill procedure which kit comprises the following components:

(a) a supply of the polar liquid or mixture of polar liquids comprising the test solution;

(b) a measuring device for measuring an appropriate quantity of the test solution;

(c) a syringe for extracting a sample of lubricating oil from the compressor;

(d) a transparent container within which to mix the measured quantity of oil with the measured quantity of test solution;

(e) instructions for use of the test kit; and (f) a holder or container for components (a) to (e) of the test kit.

The present invention is not limited to the use of any specific polar liquid or liquids for use as the test solution. In practice, however, suitable polar liquids are likely to be organic liquids containing oxygen and/or nitrogen which may or may not be mixed with water to form the test solutions. Ideally, the liquids should be relatively inexpensive. Two particular combinations which the Applicants have found to be particularly suitable for use in the present invention are respectively a mixture of methanol, ethanol and water and a mixture of acetonitrile and ethanol. However, use of other polar liquids and combinations are within the scope of the present invention provided of course that they meet the requirements as specified in the foregoing definition of the method of testing according to the invention. As will be apparent, the selection, for example, of suitable proportions of polar liquid in a polar liquid mixture for use with any specific synthetic ester lubricant is a matter of mere routine experimentation.

In preparing suitable test solutions of polar liquids the Applicants have taken a level of contamination of mineral oil of approximately 3% by weight in the synthetic ester lubricant as representing the boundary between an acceptable and unacceptable level of contamination when the refrigeration system is retrofilled. Accordingly, the proportions of the polar liquids and the sample of synthetic ester lubricant to be tested have been so determined in the Applicants' specific compositions and described hereafter, that the mixture formed in the step (a) of the test method is turbid when the mineral oil concentration is above the aforementioned level and clear when it is below the aforementioned level. Obviously, there is a degree of experimental error involved in using the test method, since for example the solubilities of mineral oils are not all identical. The Applicants' experiments have been based on the use of Suniso 3GS and Suniso 5GS which are typical napthenic refrigeration compressor oils. ("SUNISO" is a trade mark). In practice the Applicants have found that by working to a nominal 3% by weight contamination limit in their experiments, actual oil contamination levels of 1.5% by weight in the synthetic ester oil always passed the test whereas an actual contamination level of 4% or above, always failed.

EXAMPLE

In Table I are shown the proportions of ethanol, methanol and water which are suitable for use as a test solution of polar liquids for testing synthetic ester lubricants of the "Icematic SW" types shown in the heading of each column of the table.

TABLE I

|  | Icematic SW22/32 | Icematic SW68 | Icematic SW100 |
| --- | --- | --- | --- |
| Ethanol (%) | 52.02 | 52.02 | 40.46 |
| Methanol (%) | 40.46 | 43.93 | 56.65 |
| Water (%) | 7.52 | 4.05 | 2.89 |
| (% by volume) |  |  |  |

The test procedure was carried out as follows:

A measured amount of 21.5 cubic centimeters of the test solution was poured into a transparent screw-lid jar and a sample of the synthetic ester lubricant containing contaminant mineral oil measuring 5 cubic centimeters was poured into the test solution of polar solvents and the jar was thoroughly shaken after the screw-lid had been tightly fastened on the jar. If the resulting mixture was cloudy then it was concluded that the refrigeration system needed to be flushed again with the relevant Icematic SW lubricant and thereafter again tested using the above-mentioned test procedure. However, if the mixture was found to be clear then it was concluded that the mineral oil contamination was sufficiently low to permit the retrofill to be carried out.

As a different example of a test solution of polar liquids a mixture of 40 cc of acetonitrile with 10 cc of ethanol can be used. In this case the appropriate proportions of the synthetic ester oil to be tested to the test solution of polar liquids is 1 to 5 by volume. A test kit based on this alternative polar liquid system also functions at the 3% contamination level referred to above.

It will be apparent that numerous variations within the general method of testing of the invention as described above are possible without departing from the scope thereof. For example, it might perhaps be considered appropriate in some retrofill situations to apply a more stringent and lower level of mineral oil contamination in which case of course the proportions of test solution, the ingredients thereof, and/or its proportion with the synthetic ester lubricant sample would need to be adjusted accordingly. On the other hand in other cases a less stringent and higher level of mineral oil contamination may be tolerable. In Table 2 are shown the results of tests using four different test solutions designated as A, B, C, and D with a synthetic ester oil (Icematic SW 32) contaminated with varying percentage weights of the mineral oil Suniso 3GS. Thus it is seen from the Table that test solution A is suitable to detect an oil contamination level of greater than 1%, Solution B a contamination level of greater than 3%, Solution C a contamination level of greater than 5% and solution D a contamination level of greater than 10%.

TABLE 2

| % Suniso 3GS in Icematic SW 32 (w/w) | Solution A (1%) | Solution B (3%) | Solution C (5%) | Solution D (10%) |
| --- | --- | --- | --- | --- |
| 0.5 | Clear | Clear | Clear | Clear |
| 1.5 | Turbid | Clear | Clear | Clear |
| 2 | Turbid | Clear | Clear | Clear |
| 4 | Turbid | Turbid | Clear | Clear |
| 8 | Turbid | Turbid | Turbid | Clear |
| 20 | Turbid | Turbid | Turbid | Turbid |

| | % BY VOLUME | | | |
| --- | --- | --- | --- | --- |
|  | Methanol | Ethanol | Water | Ratio Oil Solvent |
| Solution A | 28.50 | 62.68 | 8.82 | 0.228 |
| Solution B | 46.24 | 46.24 | 7.52 | 0.231 |
| Solution C | 47.06 | 47.06 | 5.88 | 0.235 |
| Solution D | 73.17 | 24.39 | 2.44 | 0.244 |

Such variations are by mere routine experimentation and the resulting method of testing will, it will be appreciated, still fall within the scope of the inventive concept of the present invention as claimed in the following claims.

We claim:

1. A method of testing for contaminating mineral oil in a sample of synthetic ester lubricating oil from mechanical vapor recompression type heat transfer equipment in a system which is to be retrofilled with replacement hydrohalocarbon working fluid, which method comprises:

(a) mixing a predetermined quantity of the synthetic ester lubricating oil contaminated with mineral oil with a predetermined quantity of a polar liquid or a mixture of polar, liquids, the ester lubricating oil being itself completely miscible with the polar liquid(s) and the resulting mixture having the physical property of manifesting a discontinuous change in optical appearance between turbidity when saturated with mineral oil and clarity when unsaturated with mineral oil; the quantities of the ester lubricating oil and polar liquid(s) being so selected that the resulting mixture is just saturated with the contaminating mineral oil when the concentration of the mineral oil in the synthetic ester lubricant corresponds to the maximum which is tolerable in the operating heat transfer equipment and system after retrofilling with hydrohalocarbon working fluid; and (b) determining whether the resulting mixture is optically clear or turbid, a clear mixture indicating non-saturation and that the concentration of contaminating mineral oil in the synthetic ester lubricant is at or below the maximum tolerable concentration and that the heat transfer equipment and system can therefore be safely retrofilled with the hydrohalocarbon working fluid; and a turbid mixture indicating saturation and that the concentration of contaminating mineral oil is above the maximum tolerable concentration and that the system must therefore be reflushed with synthetic ester lubricant to further reduce the mineral oil concentration.

2. A method as claimed in claim 1, wherein the synthetic ester lubricant is an ester or mixture of esters of pentaerythitol or dipentaerythitol with one or more mono or dicarboxylic acids.

3. A method as claimed in claim 1, wherein the polar liquids comprise one or more organic liquids containing oxygen and/or nitrogen.

4. A method as claimed in claim 3, wherein the polar liquids comprise a mixture of methanol, ethanol and water.

5. A method as claimed in claim 3, wherein the polar liquids comprise a mixture of acetonitrile and ethanol.

6. A procedure for retrofilling a mechanical vapor recompression type heat transfer system with a hydrohalocarbon working fluid which procedure comprises:

(i) isolating the compressor from the remainder of the system;

(ii) draining the mineral oil from the compressor;

(iii) filling the compressor with a synthetic ester lubricating oil;

(iv) operably reconnecting the compressor to the remainder of the system;

(v) running the system to flush contaminant mineral oil back to and into the compressor, thus diluting the concentration of mineral oil in the compressor and total system;

(vi) extracting a sample of the lubricating oil from the compressor; and (vii) testing the sample of oil by the method of testing as claimed in claim 1.

7. A test kit for use in the method of testing as claimed in claim 1 which test kit comprises the following components:

(a) supply of the polar liquid or mixture of polar liquids comprising the test solution;

(b) a measuring device for measuring an appropriate quantity of the test solution;

(c) a syringe for extracting a sample of lubricating oil from the compressor;

(d) a transparent container within which to mix the measured quantity of oil with the measured quantity of test solution;

(e) instructions for use of the test kit; and (f) a holder or container for components (a) to (e) of the test kit.

8. Use of a test kit as claimed in claim 7 in a procedure for retrofilling a mechanical vapour recompression heat transfer system 9. A method as claimed in claim 2, wherein the polar liquids comprise one or more organic liquids containing oxygen and/or nitrogen.

10. A test kit as claimed in claim 7, wherein the synthetic ester lubricant is an ester or mixture of esters of pentaerythitol or dipentaerythitol with one or more carboxylic acids.

11. A test kit as claimed in claim 7, wherein the polar liquids comprise one or more organic liquids containing oxygen and/or nitrogen.

12. A test kit as claimed in claim 11, wherein the polar liquids comprise a mixture of methanol, ethanol and water.

13. A test kit as claimed in claim 12, wherein the polar liquids comprise a mixture of acetonitrile and ethanol.

\* \* \* \* \*